US012779150B2

(12) United States Patent
Hubert et al.

(10) Patent No.: US 12,779,150 B2
(45) Date of Patent: Nov. 3, 2026

(54) DRUG DELIVERY SYSTEMS AND METHODS AND DRUG PRODUCTS

(71) Applicant: JANSSEN PHARMACEUTICA NV, Beerse (BE)

(72) Inventors: Emma Louise Hubert, San Jose, CA (US); Hong Yan, Livermore, CA (US); David Ramos, Orange Park, FL (US); Shagun Popli, Pleasanton, CA (US); Steven M. Vesole, San Bruno, CA (US); Jingli Wang, San Jose, CA (US); Michael Cannamela, Atlantic Highland, NJ (US); Dolores Perez, Eaton, PA (US); Jimmy Vinh Hoang Cassebee, Fremont, CA (US)

(73) Assignee: Janssen Pharmaceutica NV, Beerse (BE)

( * ) Notice: Subject to any disclaimer, the term of this patent is extended or adjusted under 35 U.S.C. 154(b) by 893 days.

(21) Appl. No.: 18/023,632

(22) PCT Filed: Sep. 1, 2021

(86) PCT No.: PCT/EP2021/074152
§ 371 (c)(1),
(2) Date: Feb. 27, 2023

(87) PCT Pub. No.: WO2022/049136
PCT Pub. Date: Mar. 10, 2022

(65) Prior Publication Data

US 2023/0310767 A1 Oct. 5, 2023

Related U.S. Application Data

(60) Provisional application No. 63/073,033, filed on Sep. 1, 2020.

(51) Int. Cl.
*A61M 15/08* (2006.01)
*A61M 11/00* (2006.01)
*A61M 15/00* (2006.01)

(52) U.S. Cl.
CPC .......... *A61M 15/08* (2013.01); *A61M 11/007* (2014.02); *A61M 15/0003* (2014.02); *A61M 15/0035* (2014.02)

(58) Field of Classification Search
CPC ................ A61M 15/08; A61M 11/007; A61M 15/0003; A61M 15/0035
(Continued)

(56) References Cited

U.S. PATENT DOCUMENTS 4,946,069 A 8/1990 Fuchs
5,823,183 A * 10/1998 Casper ............. A61M 15/0091 128/200.24

(Continued)

FOREIGN PATENT DOCUMENTS

CA 2020425 A1 1/1991
FR 2970955 A1 8/2012

(Continued)

OTHER PUBLICATIONS

International Search Report and Written Opinion received for PCT Application No. PCT/EP2021/074152, mailed on Jan. 10, 2022, 25 pages.

*Primary Examiner* — Phillip A Gray
(74) *Attorney, Agent, or Firm* — Craig M. Brown

(57) ABSTRACT

Various exemplary drug holders (102, 200) for drug delivery devices (100), drug products utilizing the same, and methods of using drug holders for drug delivery devices are provided. In general, a nasal drug delivery device is configured to dispense therefrom at least one dose of a drug therefrom into a nose. The drug delivery device includes a drug holder that (Continued)

contains the drug therein that is delivered out of the drug delivery device. The drug holder can include two cavities (208, 210) therein that are fluidically sealed from one another prior to use of the drug delivery device to cause drug delivery. A first one of the cavities includes the drug therein, and a second one of the cavities includes a drug or air therein.

31 Claims, 9 Drawing Sheets

(58) Field of Classification Search
USPC .............................................................. 604/48
See application file for complete search history.

(56) References Cited

U.S. PATENT DOCUMENTS

| | | | |
|---|---|---|---|
| 6,708,846 | B1 | 3/2004 | Fuchs et al. |
| 7,258,119 | B2 | 8/2007 | Mazzoni |
| 9,089,658 | B2 | 7/2015 | Dunne et al. |
| 9,555,950 | B2 | 1/2017 | Maner et al. |
| 2005/0256182 | A1 | 11/2005 | Sutter et al. |
| 2016/0354558 | A1 | 12/2016 | Seguin et al. |
| 2018/0361085 | A1 | 12/2018 | Malhotra et al. |
| 2020/0197630 | A1 | 6/2020 | Petit |
| 2020/0197633 | A1 | 6/2020 | Shahaf et al. |

FOREIGN PATENT DOCUMENTS

| | | | |
|---|---|---|---|
| WO | 2015025324 | A1 | 2/2015 |
| WO | 2020069559 | A1 | 4/2020 |

* cited by examiner

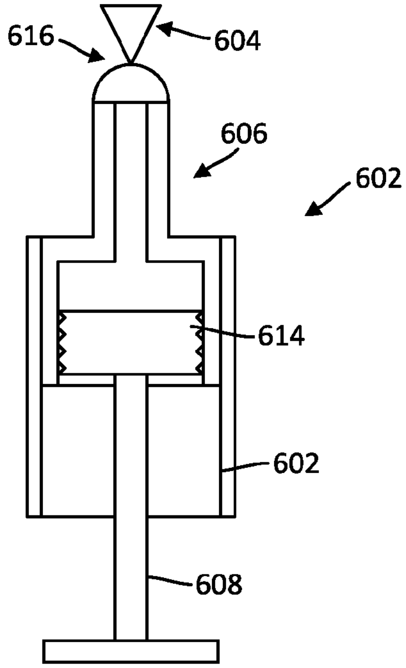
*FIG. 8*
*FIG. 9*
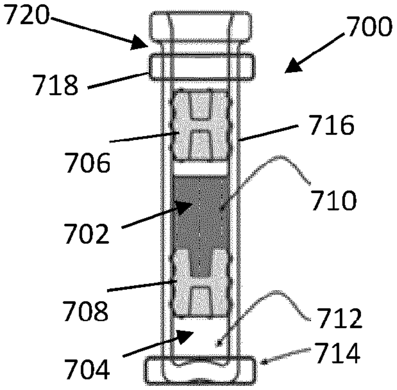

DRUG DELIVERY SYSTEMS AND METHODS AND DRUG PRODUCTS

CROSS REFERENCE TO RELATED APPLICATIONS

This application is the U.S. national stage of PCT Application No. PCT/EP2021/074152, filed Sep. 1, 2021, which claims priority to U.S. Provisional Patent Application No. 63/073,033, filed Sep. 1, 2020, the entire contents of each of which are hereby incorporated by reference as if set forth in their entirety herein.

FIELD

The present disclosure relates generally to drug holders for drug delivery devices and drug products utilizing the same.

BACKGROUND

There are many different ways in which a drug can be administered to a user. Depending on the drug, intranasal drug delivery can be one of the most effective ways to achieve desired clinical benefits in a timely manner and in a manner that is convenient and comfortable for a patient.

Intranasal drug administration is a non-invasive route for drug delivery. Since the nasal mucosa offers numerous benefits as a target tissue for drug delivery, a wide variety of drugs may be administered by intranasal systemic action. Moreover, intranasal drug delivery can avoid the risks and discomfort associated with other routes of drug delivery, such as intravenous drug delivery, and can allow for easy self-administration.

Generally, to maximize the efficacy of the drug through intranasal administration, the majority volume of the aerosolized dose of the drug needs to reach the correct region of the nasal cavity. As such, additional measures may need to be taken for effective intranasal drug delivery. For example, the user may need to have a clear nostril, tilt their head back at approximately 45°, close the opposite nostril, and then sniff gently while the dose of drug is administered. In order to coordinate these measures, and given that nasal administration is intimate, self-administration by the user may be desired. Further, due to the nasal cycle (alternating physiological partial congestion of the nasal turbinate to facilitate nasal function) or pathological congestion, one nostril is likely to provide a more effective drug delivery route than the other nostril at any given time. As such, it is desired that an equal dose of the drug be delivered to each nostril of the user to inhibit under-dosing of the drug.

Dual-dose intranasal drug delivery devices are available that are designed for self-administration of two distinct aerosolized sprays, one for each nostril, that together constitute one dose of drug. These devices require a series of operational steps that the user needs to properly carry out to effect optimal drug delivery through self-administration. After the drug is delivered, the device may be disposed of as a used device for recycling or as medical waste. However, the device can have a residual amount of the drug remaining in the device that cannot be further delivered from the device. The residual drug may not be intended by the device manufacturer and/or the drug prescriber to be accessed by a person, but the residual drug may nevertheless be accessed, e.g., by accident or by breaking the device to access the residual drug. Thus, the residual drug may be accessed by an unauthorized person, such as a child, a person not prescribed the drug, etc., who could be harmed by the drug and/or attempt its unauthorized use. Preventing access to the residual drug may be particularly important for controlled substances that could be abused and/or be more likely than other drugs to lead to an addiction.

Accordingly, there remains a need for improved nasal drug delivery devices.

SUMMARY

In general, drug holders for drug delivery devices, drug products utilizing the same, and methods of using drug holders for drug delivery devices are provided.

In one aspect, a drug delivery system is provided that in one embodiment includes a drug holder configured to be coupled to a drug delivery device. The drug holder includes a first cavity configured to contain either a first drug or air therein, a second cavity configured to contain either a first drug or air therein, and a seal member located between the first and second cavities, configured to provide a fluid seal between the first and second cavities, and configured to be broken by a nasal drug delivery device to break the fluid seal.

The drug delivery system can vary in any number of ways. For example, the drug holder can also include a head portion and a body portion that is distal to the head portion, the first and second cavities can each be in the body portion, and the seal member can be located in the body portion between the first and second cavities.

For another example, the drug holder can be a vial.

For still another example, the first cavity can contain the first drug, and the second cavity can contains the second drug. The first drug can be one of ketamine, esketamine, naloxone, and sumatriptan, the second drug can be one of ketamine, esketamine, naloxone, and sumatriptan, and the first and second drugs can be the same or can be different. A drug delivery method can include actuating the drug delivery device to cause a plunger to push the first drug out of an opening formed in the drug delivery device, and, after the first drug has been pushed out of the opening, actuating the drug delivery device again to cause the plunger to push the second drug out of the opening.

For yet another example, the drug delivery system can also include the nasal drug delivery device, and the seal member can be configured to be broken by being pierced or punctured by at least one of a piston, a pin, and a needle of the nasal drug delivery device.

In another aspect, a drug product is provided that in one embodiment includes a drug product disposed in a drug holder The drug holder is configured to be coupled to a drug delivery device. The drug holder includes a head portion, a body portion that is distal to the head portion, a first cavity in the body portion that is configured to contain either the drug product or air therein, a second cavity in the body portion that is configured to contain either the drug product or air therein, and a seal member located in the body portion between the first and second cavities, configured to provide a fluid seal between the first and second cavities, and configured to be broken by a nasal drug delivery device to break the fluid seal. The drug product is one of ketamine, esketamine, naloxone, and sumatriptan. The drug holder can have any number of variations.

For another example, the first cavity can contain the first drug, the second cavity can contain air, and the first cavity can be distal to the second cavity. The first drug can be one of ketamine, esketamine, naloxone, and sumatriptan. A drug delivery method can include actuating the drug delivery device to cause a plunger to push both the first drug and the air out of an opening formed in the drug delivery device.

For yet another example, the first cavity can contain air, the second cavity can contain the second drug, and the first cavity can be distal to the second cavity. The second drug can be one of ketamine, esketamine, naloxone, and sumatriptan. A drug delivery method can include actuating the drug delivery device to cause a plunger to push both the second drug and the air out of an opening formed in the drug delivery device.

For still another example, the drug delivery system can also include a second seal member located proximal to the first and second cavities and configured to be broken by a drug delivery device to break a fluid seal provided by the second seal member.

For another example, the drug delivery system can include the nasal drug delivery device, the drug delivery device can include a tip configured to be positioned in a nose of a patient, and the tip can have an opening therein. In some embodiments, the first cavity can contain the first drug, the second cavity can contain the second drug, and the drug delivery device can include an actuator that is configured to be actuated in a first actuation to cause delivery of the first drug through the opening without causing delivery of the second drug through the opening, and that is configured to be actuated in a second actuation to cause delivery of the second drug through the opening. The first drug can be one of ketamine, esketamine, naloxone, and sumatriptan, the second drug can be one of ketamine, esketamine, naloxone, and sumatriptan, and the first and second drugs can be the same or can be different. In some embodiments, the first cavity can contain the first drug, the second cavity can contain air, and the drug delivery device can be configured to simultaneously deliver the first drug and the air through the opening. The first drug can be one of ketamine, esketamine, naloxone, and sumatriptan.

In another embodiment, a drug delivery system includes a drug holder and a nasal drug delivery device. The drug holder includes a first blister seal and a second blister seal. The drug holder is configured to hold a drug between the first and second blister seals. The first blister seal is distal to the second blister seal. The nasal drug delivery device includes a proximal tip configured to be positioned in a nose of a patient. The tip has an opening therein. The nasal drug delivery device also includes an actuator configured to be actuated to break the first blister seal and thereby create a force that causes the second blister seal to break and the drug to be delivered out of the opening.

The drug delivery system can vary in any number of ways. For example, the actuator can include a plunger configured to be actuated by moving proximally relative to the proximal tip. The drug holder can be located between the opening and the plunger.

For another example, the drug can be one of ketamine, esketamine, naloxone, and sumatriptan.

In another aspect, a drug product is provided that in one embodiment includes a drug product disposed in a drug delivery system. The drug delivery system includes a drug holder and a nasal drug delivery device. The drug holder includes a first blister seal and a second blister seal. The drug holder is configured to hold the drug product between the first and second blister seals. The first blister seal is distal to the second blister seal. The nasal drug delivery device includes a proximal tip configured to be positioned in a nose of a patient. The tip has an opening therein. The nasal drug delivery device also includes an actuator configured to be actuated to break the first blister seal and thereby create a force that causes the second blister seal to break and the drug product to be delivered out of the opening. The drug product is one of ketamine, esketamine, naloxone, and sumatriptan. The drug delivery system can have any number of variations.

BRIEF DESCRIPTION OF DRAWINGS

The present invention is described by way of reference to the accompanying figures which are as follows:

FIG. 8 is a side cross-sectional view of the drug holder and drug delivery device of FIG. 6 with drug being delivered out of the drug delivery device;

FIG. 9 is a side cross-sectional view of another embodiment of a drug holder;

DETAILED DESCRIPTION

Figure 1:
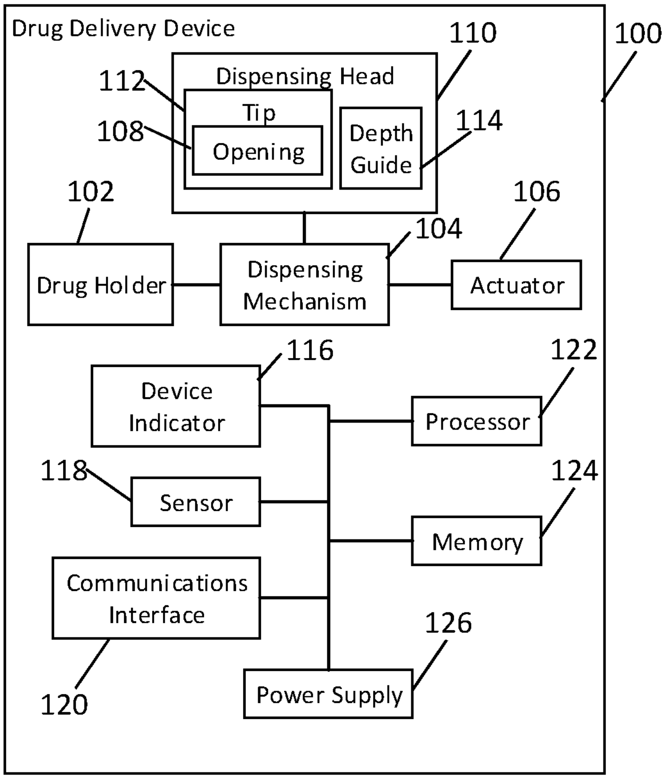
FIG. 1 is a block diagram of one embodiment of a drug delivery device.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary drug holders for drug delivery devices, drug products utilizing the same, and methods of using drug holders for drug delivery devices are provided. In general, a nasal drug delivery device is configured to dispense therefrom at least one dose of a drug therefrom into a nose. The drug delivery device includes a drug holder that contains the drug therein that is delivered out of the drug delivery device. The drug holder can include two cavities therein that are fluidically sealed from one another prior to use of the drug delivery device to cause drug delivery. A first one of the cavities includes the drug therein, and a second one of the cavities includes a drug or air therein.

In embodiments in which the second cavity includes air therein, the drug can be configured to exit the drug holder before the air exits the drug holder. The air exiting the drug holder after the drug may help ensure that substantially all of the drug has exited the drug holder such that substantially no residual drug remains in the drug holder. Having substantially no residual drug left in a drug holder after use thereof may prevent access to the drug after use of the drug holder, which may be particularly important for esketamine, ketamine, and other controlled substances that could be abused and/or be more likely than other drugs to lead to an addiction. Having substantially no residual drug left in a drug holder after use thereof may facilitate recycling of the used drug holder (alone or in combination with all or part of a drug delivery device that delivered drug from the drug holder) since substantially no drug will be present when the drug holder is recycled. Some drugs, such as esketamine, ketamine, and other controlled substances, may be required to be disposed of per a government requirement, e.g., U.S. federal Drug Enforcement Administration requirement, non-U.S. federal requirement, state requirement, or local requirement, to help, e.g., ensure that the drug is not accessed by an unauthorized person. Disposal of the used drug holder can include recycling or throwing out of the used drug holder (alone or in combination with all or part of a drug delivery device that delivered drug from the drug holder) as medical waste. Having substantially no residual drug left in a drug holder after use thereof may help satisfy the government requirement since the drug holder will be substantially free of the drug when the drug holder is disposed.

In embodiments in which the second cavity includes air therein, the air can be configured to exit the drug holder before the drug exits the drug holder. The drug exiting the drug holder after the air may help ensure that the drug reaches the correct region of the nasal cavity by being "blown" proximally by the air during drug delivery and/or may reduce or eliminate the need for the user to sniff or breathe inward during drug delivery since the air will urge the drug into the patient's nostril and to the correct region of the nasal cavity. It can be difficult and/or uncomfortable for some users with impaired respiratory function or other illness to sniff or breathe inward with sufficient force to help urge the drug into the patient's nostril and to the correct region of the nasal cavity. The drug exiting the drug holder after the air may help dry the drug faster in the user than if the air was not delivered. The user may be instructed per the drug holder's and/or drug delivery Instructions For Use (IFU) to wait a certain amount of time after drug delivery into one nostril before delivering the drug into their other nostril in order to allow sufficient time for the first-delivered drug to dry and not run out of the user's nose during the second drug delivery.

In embodiments in which each of the cavities contains a drug therein, each of the drugs can be the same such that the drug delivery device that delivers drug from the drug holder is usable to deliver subsequent doses of the same drug to a user of the drug delivery device, which may help ensure that a predictable, substantially equal amount of drug is delivered and/or may help provide a stop to end the first drug dosing.

In embodiments in which each of the cavities contains a drug therein, the drugs can be different from one another such that the drug delivery device is usable to deliver doses of different drugs to a user of the drug delivery device. The user may therefore be able to use the same drug delivery device repeatedly in fulfilling two or more drug prescriptions and/or the drug delivery device may provide for on-board mixing of the drugs prior to delivery of a mixed drug to the user.

In some embodiments, the drug holder can include a single cavity containing drug therein. In such embodiments, the drug holder can be glass and manufactured using extrusion, which may be a less expensive method of manufacturing a drug holder than other manufacturing methods such as molding, assembled without orientation, and/or may facilitate disposal of the drug holder as medical waste by including less residual drug therein after drug delivery than drug holders manufactured using other methods, and/or may facilitate recycling of the drug holder by facilitating separation of the drug holder from a remainder of the drug delivery device.

In some embodiments in which the drug holder includes two cavities or a single cavity, the drug holder can be resilient in at least a portion thereof. The resilience is configured to allow the drug holder to flex, which may help couple the drug holder to the drug delivery device or other element. Alternatively, the drug delivery device or the other element can be resilient in at least a portion thereof to help couple the drug holder to the drug delivery device or other element.

The drug to be delivered using a drug delivery device as described herein can be any of a variety of drugs. Examples of drugs that can be delivered using a drug delivery device as described herein include antibodies (such as monoclonal antibodies), hormones, antitoxins, substances for the control of pain, substances for the control of thrombosis, substances for the control of infection, peptides, proteins, human insulin or a human insulin analogue or derivative, polysaccharide, DNA, RNA, enzymes, oligonucleotides, antiallergics, antihistamines, anti-inflammatories, corticosteroids, disease modifying anti-rheumatic drugs, erythropoietin, and vaccines. Examples of drugs that can be delivered using a drug delivery device as described herein include ketamine (e.g., Ketalar®), esketamine (e.g., Spravato®, Ketanest®, and Ketanest-S®), naloxone (e.g., Narcan®), and sumatriptan (e.g., Imitrex®).

A drug delivery device configured to expel a drug into a nose of a patient and to drive delivery of the drug using a propellant can have a variety of configurations. In general, the drug delivery device is configured to deliver a drug to a patient, where the drug is provided in a defined dosage form within the drug delivery device.

FIG. 1 illustrates one embodiment of a drug delivery device 100 configured to expel a drug into a nose of a patient. As will be appreciated by a person skilled in the art, the drug delivery device 100 can include different features in different embodiments depending upon various requirements, such as the type of drug, typical dosage(s) of the drug, safety requirements in various jurisdictions, whether the device is powered, etc.

The drug delivery device 100 includes a drug holder 102 configured to contain a drug therein for delivery from the device 100 to a patient. The drug holder 102 can have a variety of configurations, such as a cartridge, a vial, a blow-fill-seal (BFS) capsule, a blister pack, etc. In an exemplary embodiment, the drug holder 102 is a vial. An exemplary vial is formed of one or more materials, e.g., glass, polymer(s), etc. In some embodiments, a vial can be formed of glass. In other embodiments, a vial can be formed of one or more polymers. In yet other embodiments, different portions of a vial can be formed of different materials. An exemplary vial can include a variety of features to facilitate sealing and storing a drug therein, as described herein and illustrated in the drawings. However, a person skilled in the art will appreciate that the vials can include only some of these features and/or can include a variety of other features known in the art. The vials described herein are merely intended to represent certain exemplary embodiments.

The drug delivery device 100 also includes a dispensing mechanism 104 that is operatively coupled to the drug holder 102 and configured to drive the drug out of device 100 from the drug holder 102. The dispensing mechanism 104 can have a variety of configurations. For example, the dispensing mechanism 104 can include a plunger configured to push the drug out of the drug holder 102. For another example, the dispensing mechanism 104 can include a piston, pin, and/or a needle configured to pierce through or puncture a seal member of the drug holder 102 in embodiments in which the drug holder 102 includes a pierceable or puncturable seal member.

The drug delivery device 100 also includes an actuator 106 configured to be actuated by a user to cause the dispensing mechanism 104 to begin delivering a dose of the drug through an opening or nozzle 108 in the drug delivery device 100. In an exemplary embodiment, the drug delivery device 100 is configured to be self-administered such that the user who actuates the actuator 106 is the patient receiving the drug from the drug delivery device 100, although another person can actuate the device 100 for delivery into another person. The actuator 106 can have a variety of configurations, as discussed further below. For example, the actuator 106 can include a plunger. For another example, the actuator 106 can include a pressable button. For still another example, the actuator 106 can include a movable switch. For yet another example, the actuator 106 can include a squeezable body of the drug holder 102.

The opening 108 through which the drug exits the drug delivery device 100 is formed in a dispensing head 110 of the drug delivery device 100 in a tip 112 of the dispensing head 110. The tip 112 is configured to be inserted into a nostril of a patient. In an exemplary embodiment, the tip 112 is configured to be inserted into a first nostril of the patient during a first stage of operation of the drug delivery device 100 and into a second nostril of the patient during a second stage of operation of the drug delivery device 100. The first and second stages of operation involve two separate actuations of the actuator 106, a first actuation corresponding to a first dose of the drug being delivered and a second actuation corresponding to a second dose of the drug being delivered. The dispensing head 110 includes a depth guide 114 configured to contact skin of the patient, e.g., between the patient's first and second nostrils, such that a longitudinal axis of the dispensing head 110 is substantially aligned with a longitudinal axis of the nostril in which the tip 112 is inserted. A person skilled in the art will appreciate that the longitudinal axes may not be precisely aligned but nevertheless be considered to be substantially aligned due to any number of factors, such as manufacturing tolerances and sensitivity of measurement equipment.

In an exemplary embodiment, the dispensing head 110 has a tapered shape in which the dispensing head 110 has a smaller diameter at its distal end than at its proximal end where the opening 108 is located. The opening 108 having a relatively small diameter facilitates spray of the drug out of the opening 108, as will be appreciated by a person skilled in the art. A spray chamber through which the drug is configured to pass before exiting the opening 108 is located within a proximal portion of the tapered dispensing head 110, distal to the opening 108. When the drug passes through the spray chamber at speed, the spray chamber facilitates production of a fine mist that exits through the opening 108 with a consistent spray pattern.

In some embodiments, the dispensing head 110 can include two tips 112 each having an opening 108 therein such that the drug delivery device 100 is configured to simultaneously deliver doses of drug into two nostrils in response to a single actuation of the actuator 106.

The drug delivery device 100 also includes a device indicator 116 configured to present information to a user about a status of the drug delivery device 100 and/or the drug contained in the drug holder 102. The device indicator 116 can be a visual indicator, such as a display screen, one or more lights, one or more colored and/or numbered markings, etc. Alternatively or in addition, the device indicator 116 can be an audio indicator configured to provide sound.

The drug delivery device 100 also includes a sensor 118 configured to sense information relating to the drug delivery device 100 and/or the drug contained in the drug holder 102. Examples of information that the sensor 118 can sense include environmental conditions (e.g., temperature, humidity, geographic location, time, etc.). The drug delivery device 100 can also include a communications interface 120 configured to communicate externally data which has been gathered by the sensor 118 about the drug delivery device 100 and/or the drug contained in the drug holder 102, which may facilitate analysis regarding the patient's treatment, patient compliance, use of the drug delivery device 100, etc.

In embodiments in which the drug delivery device 100 includes one or more electrical components, e.g., the device indicator 116 (which in some embodiments can be powered while in other embodiments not be powered), the sensor 118, the communications interface 120, a processor 122, a memory 124, etc., the drug delivery device 100 includes a power supply 126 configured to deliver electrical power to the one or more electrical components of the drug delivery device 100. The power supply 126 can be a source of power which is integral to drug delivery device 100 and/or can be a mechanism configured to connect the drug delivery device 100 to an external source of power. The processor 122 is configured to receive gathered data from the sensor 118 and to cause the data to be stored in the memory 124, to be indicated on the device indicator 110, and/or and to be communicated externally via the communications interface 120. The memory 124 is configured to store instructions that are configured to be executed by the processor 122 for the processor 122 to process information regarding the various electrical components with which the processor 122 is in communication.

As mentioned above, the drug delivery device 100 can include different features in different embodiments depending upon various requirements. For example, the drug delivery device 100 can omit any one or more of the depth guide 114, the device indicator 116, the sensor 118, the communications interface 120, the processor 122, the memory 124, and the power supply 126.

Figure 2:
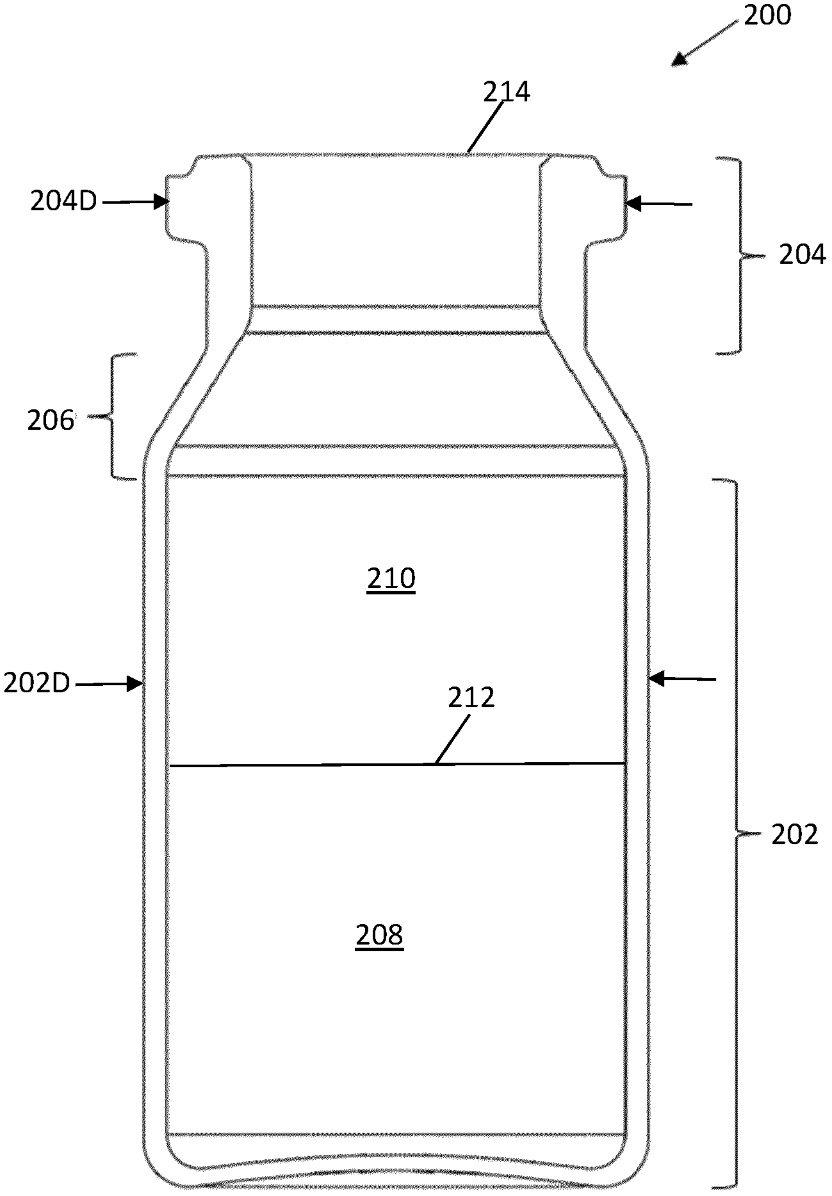
FIG. 2 is a side cross-sectional view of one embodiment of a drug holder.

FIG. 2 illustrates an exemplary embodiment of the drug holder 102 of FIG. 1 in the form of a vial 200 that is configured to be used with the drug delivery device 100 of FIG. 1. The vial 200 includes a base or distal portion 202 and a head or proximal portion 204. As shown, the vial 200 also includes an inwardly tapering neck portion 206 that extends between the base portion 202 and the head portion 204. The inwardly tapering neck portion 206 allows the head portion 204 to have a maximum outer diameter 204D that is less than a maximum outer diameter 202D of the base portion 202. In other embodiments, the taper between the base and head portions 202, 204 can be omitted, and the base and head portions 302, 304 can have a same maximum outer diameter 202D, 204D as one another.

The base portion 202 defines a distal cavity 208 within the base portion 202. The base portion 202 also defines a proximal cavity 210 within the base portion 202. In some embodiments, air is contained in the distal cavity 208, and a drug is contained in the proximal cavity 210. In this way, the drug can exit the vial 200 for delivery to a user followed by exit of the air from the vial 200 for delivery to the user. As discussed above, the air exiting the vial 200 after the drug may help ensure that substantially all of the drug has exited the drug holder 200 such that substantially no residual drug remains in the drug holder 200. A person skilled in the art will appreciate that the amount of residual drug may not be precisely zero but nevertheless be considered to be substantially none due to any number of factors, such as sensitivity of measurement equipment. Having substantially no residual drug left in a drug holder after use thereof may prevent access to the drug after use of the drug holder, which may be particularly important for esketamine, ketamine, and other controlled substances. Having substantially no residual drug left in a drug holder after use thereof may facilitate recycling of the used drug holder (alone or in combination with all of part of a drug delivery device that delivered drug from the drug holder) since substantially no drug will be present when the drug holder is recycled. Some drugs, such as esketamine, ketamine, and other controlled substances, may be required to be disposed of per a government requirement to help, e.g., ensure that the drug is not accessed by an unauthorized person. Disposal of the used drug holder can include recycling or throwing out of the used drug holder (alone or in combination with all of part of a drug delivery device that delivered drug from the drug holder) as medical waste. Having substantially no residual drug left in a drug holder after use thereof may help satisfy the government requirement since the drug holder will be substantially free of the drug when the drug holder is disposed.

In other embodiments, air is contained in the proximal cavity 210, and a drug is contained in the distal cavity 208. In this way, the air can exit the vial 200 for delivery to a user followed by exit of the drug from the vial 200 for delivery to the user. As discussed above, the drug exiting the vial 200 after the air may help ensure that the drug reaches the correct region of the nasal cavity by being drawn proximally by the air moving proximally during drug delivery and/or may reduce or eliminated the need for the user to sniff or breathe inward during drug delivery since the air will urge the drug into the patient's nostril and to the correct region of the nasal cavity. It can be difficult and/or uncomfortable for some users with impaired respiratory function or other illness to sniff or breathe inward with sufficient force to help urge the drug into the patient's nostril and to the correct region of the nasal cavity. The drug exiting the vial 200 after the air may help dry the drug faster in the user than if the air was not delivered. The user may be instructed per the drug holder's and/or drug delivery IFU to wait a certain amount of time, e.g., three minutes, five minutes, etc., after drug delivery into one nostril before delivering the drug into their other nostril in order to allow sufficient time for the first-delivered drug to dry and not run out of the user's nose during the second drug delivery.

In still other embodiments, a first drug is contained in the distal cavity 208, and a second drug is contained in the proximal cavity 210. In an exemplary embodiment, the first and second drugs are the same such that the drug delivery device that delivers drug from the drug holder 200 is usable to deliver subsequent doses of the same drug to a user of the drug delivery device. As discussed above, a drug holder having two drug chambers each with a drug contained therein may help ensure that a predictable, substantially equal amount of drug is delivered in each of the first and second stages of operation and/or may help provide a stop to end the first stage of operation. A person skilled in the art will appreciate that the drug amounts may not be precisely equal but nevertheless be considered to be substantially equal due to any number of factors, such as sensitivity of measurement equipment. In another exemplary embodiment, the first and second drugs are not the same as one another such that the drug delivery device is usable to deliver doses of different drugs to a user of the drug delivery device. The user may therefore be able to use the same drug delivery device repeatedly in fulfilling two or more drug prescriptions and/or the drug delivery device 200 may provide for on-board mixing of the first and second drug prior to delivery of the mixed first and second drugs to the user.

The vial 200 includes a first seal member 214 configured to provide a fluid tight seal at a proximal end of the proximal cavity 210 until the seal provided by the first seal member 214 is broken. The first seal member 214 is located in the head portion 204 of the vial 200 in this illustrated embodiment but can instead be located in the base portion 202. The seal provided by the first seal member 214 can be broken in a variety of ways, such as by being pierced by a needle, pin, piston, etc. of the drug delivery device to which the vial 200 is coupled. The first seal member 214 can have a variety of configurations, as will be appreciated by a person skilled in the art, such as by being a pierceable polymer septum or a foil layer. The first seal member 214 can be protected from accidental puncturing or piercing before intended use with a removable protective member or stopper, such as a tamper evident (TE) seal, etc. located at the proximal end of the vial 200.

The distal and proximal cavities 210, 208 are isolated from one another in an initial state of the vial 200. The vial 200 includes a second seal member 212 that is located in the base portion 202. The second seal member 212 is configured to provide a fluid tight seal such that the drug in the distal cavity 210 and the air in the proximal cavity 208 are separated from each other until the seal provided by the second seal member 212 is broken. The seal provided by the second seal member 212 can be broken in a variety of ways, such as by being pierced by a needle, pin, piston, etc. of the drug delivery device to which the vial 200 is coupled, such as the same needle, pin, piston, etc. that breaks the first seal member 214. The second seal member 212 can have a variety of configurations, as will be appreciated by a person skilled in the art, such as by being a pierceable polymer septum or a foil layer.

The first seal member 214 is proximal to both of the distal and proximal cavities 210, 210. The second seal member 212 is located between the distal and proximal cavities 210, 208, e.g., is distal to the proximal cavity 210 and is proximal to the distal cavity 208, such that the distal and proximal cavities 210, 208 are isolated from each other prior to piercing or puncturing of the second seal member 212. The second seal member 212 can be configured to facilitate stopping the first stage of operation by providing a surface against which a piston, pin, needle, or other piercing element abuts at the end of the first stage of operation.

While the base portion 202 can have a variety of configurations, in this illustrated embodiment, the base portion 202 has a substantially cylindrical shape. In other embodiments, the base portion 202 can have any other suitable shapes, e.g., a substantially rectangular shape, etc. A person skilled in the art will appreciate that a shape may not be a precise shape (e.g., a precise cylinder or a precise rectangle) but nevertheless be considered to be substantially that shape due to any number of factors, such as manufacturing tolerances and sensitivity of measurement equipment.

Figure 3:
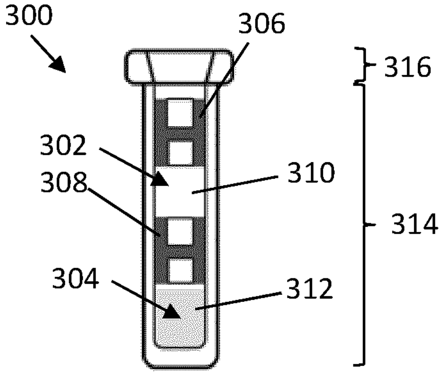
FIG. 3 is a side cross-sectional view of another embodiment of a drug holder.

FIG. 3 illustrates another exemplary embodiment of the drug holder 102 of FIG. 1 that is configured to be used with the drug delivery device 100 of FIG. 1. The drug holder 300 in this illustrated embodiment is a vial and is generally configured and used similar to the drug holder 200 of FIG. 2 and includes a proximal cavity 302 configured to contain air or a drug therein, a distal cavity 304 configured to contain air or a drug therein, a first seal member 306, and a second seal member 308. FIG. 3 illustrates air 310 in the proximal cavity 302 and a drug 312 in the distal cavity 304. The drug holder 300 in this illustrated embodiment includes a base portion 314 and a head portion 316 that has a larger maximum outer diameter than the base portion 314, though the drug holder 30 does not include a tapered neck portion.

Figure 4:
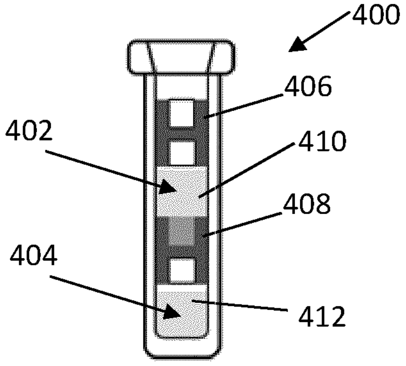
FIG. 4 is a side cross-sectional view of yet another embodiment of a drug holder.

FIG. 4 illustrates another exemplary embodiment of the drug holder 102 of FIG. 1 that is configured to be used with the drug delivery device 100 of FIG. 1. The drug holder 400 in this illustrated embodiment is a vial and is generally configured and used similar to the drug holder 200 of FIG. 2 and includes a proximal cavity 402 configured to contain air or a drug therein, a distal cavity 404 configured to contain air or a drug therein, a first seal member 406, and a second seal member 408. FIG. 4 illustrates a first drug 410 in the proximal cavity 402 and a second drug 412 in the distal cavity 404. As mentioned above, the first and second drugs 410, 412 can be the same as each other or different from one another.

Figure 5:
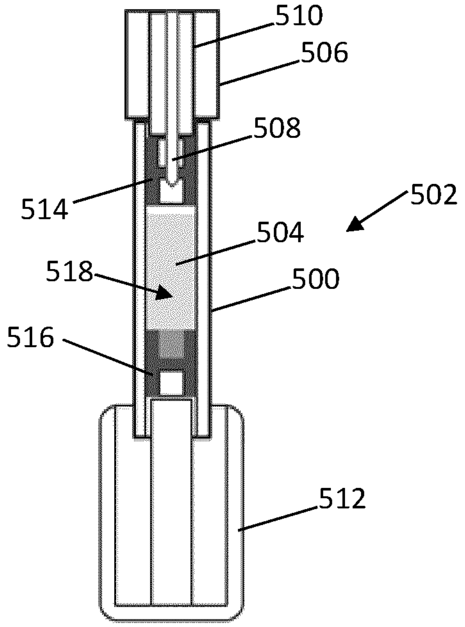
FIG. 5 is a side cross-sectional view of still another embodiment of a drug holder and another embodiment of the drug delivery device.
Figure 5A:
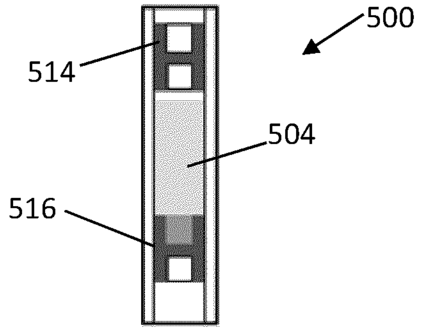
FIG. 5A is a side cross-sectional view of the drug holder of FIG. 5.

FIGS. 5 and 5A illustrate another exemplary embodiment of the drug holder 102 of FIG. 1 that is configured to be used with the drug delivery device 100 of FIG. 1. The drug holder 500 in this illustrated embodiment is a vial. FIG. 5 also illustrates a drug delivery device 502 that is configured to deliver a drug 504 from the drug holder 500 and is generally configured and used similar to the drug delivery device 100 of FIG. 1. FIG. 5 illustrates a dispensing head 506, a needle 508, a needle holder 510 that holds the needle 508 and is fixed to the dispensing head 506, and an actuator 512 of the drug delivery device 502, which in this illustrated embodiment includes a plunger. FIG. 5A illustrates the vial 500 as a standalone element.

The vial 500 in this illustrated embodiment is an extruded vial that is formed of an extruded piece of glass with first and second seal members 514, 516 at distal and proximal ends of the vial 500, respectively. The first seal member 514 is configured to be pierced or punctured by the needle 508 when the drug holder 502 is coupled to the drug delivery device 500, whether so coupled by a user of the drug delivery device 500 or during manufacturing of the drug delivery device 500. The second seal member 516 is configured to be pushed toward the first seal member 514 to cause drug delivery in response to actuation of the actuator 512, e.g., by a user pushing on an external surface of the actuator 512. Forming the vial 500 via extrusion may be a less expensive method of manufacturing a vial than other manufacturing methods such as molding and/or may facilitate disposal of the vial 500 as medical waste by including less residual drug therein after drug delivery than vials manufactured using other methods, and/or may facilitate recycling of the vial 500 by facilitating separation of the vial 500 from a remainder of the drug delivery device 502.

The vial 500 in this illustrated embodiment is a single-chamber vial that includes a single chamber 518 containing the drug 504 therein. The drug delivery device 502 in this illustrated embodiment is thus configured to deliver a single drug dose.

Figure 6:
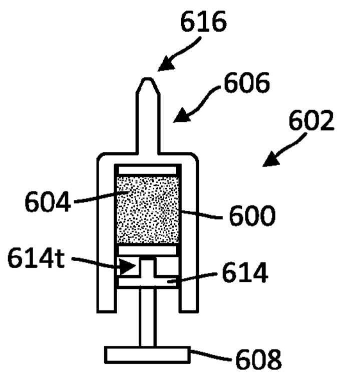
FIG. 6 is a side cross-sectional view of another embodiment of a drug holder and a portion of another embodiment of the drug delivery device.
Figure 7:
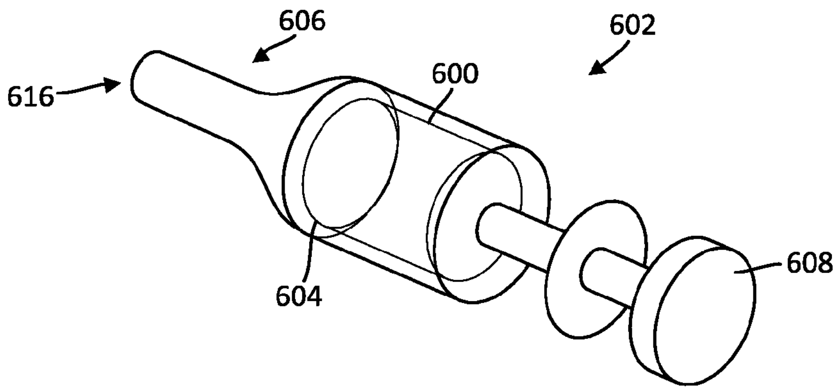
FIG. 7 is a perspective view of the drug holder and drug delivery device of FIG. 6.

FIGS. 6 and 7 illustrate another exemplary embodiment of the drug holder 102 of FIG. 1 that is configured to be used with the drug delivery device 100 of FIG. 1. The drug holder 600 in this illustrated embodiment is a blister pack. FIGS. 6 and 7 also illustrate a drug delivery device 602 that is configured to deliver a drug 604 from the drug holder 600. FIGS. 6 and 7 illustrates a dispensing head 606 and an actuator 608 of the drug delivery device 602, which in this illustrated embodiment includes a plunger. The drug delivery device 600 and the drug holder 602 are generally configured and used similar to the drug delivery device 502 and the drug holder 500 of FIG. 5. However, in this illustrated embodiment, the drug holder 600 includes first and second seal members 610, 612 at distal and proximal ends of the drug holder 600, respectively, that seal either end of the blister pack 600.

In an exemplary embodiment of using the drug delivery device 602, the proximal seal member 612 is configured to be pierced or punctured by the actuator 608, e.g., a distal tip 614*t* of a distal stopper 614, in response to actuation of the actuator 608, e.g., by a user pushing on an external surface of the actuator 608. The proximal seal member 612 bursts as a blister in response to being pierced or punctured. A force created by the bursting of the proximal seal member 612 urges the drug 604 proximally toward the first seal member 610, which causes the distal seal member 610 to burst as a blister. The force created by the bursting of the distal seal member 610, in combination with any remaining force created by the bursting of the proximal seal member 612, causes the drug 604 to be sprayed out of an opening 616 formed in the dispensing head 606, as shown in FIG. 8.

FIG. 9 illustrates another exemplary embodiment of the drug holder 102 of FIG. 1 that is configured to be used with the drug delivery device 100 of FIG. 1. The drug holder 700 in this illustrated embodiment is a vial and is generally configured and used similar to the drug holder 200 of FIG. 2 and includes a proximal cavity 702 configured to contain air or a drug therein, a distal cavity 704 configured to contain air or a drug therein, a first seal member 706, and a second seal member 708. FIG. 9 illustrates a first drug 710 in the proximal cavity 702 and air 712 in the distal cavity 704.

The vial 700 includes a distal flange 714 configured to facilitate handling of the vial 700. The distal flange 714 is configured to facilitate proximal pushing of the vial 700 by providing an enlarged distal surface area for pushing the vial 700 proximally, whether the distal flange 714 is being pushed by a user, e.g., with a finger or thumb, or by an actuator or other element of a drug delivery device. The distal flange 714 is configured to facilitate distal pulling of the vial 700 by providing an area to grip that extends radially outward of a body 716 of the vial 700, whether the distal flange 714 is being pulled by a user, e.g., with a finger or thumb, or by an actuator or other element of a drug delivery device.

The vial 700 includes a proximal flange 718 configured to facilitate handling of the vial 700. The proximal flange 718 is configured to facilitate coupling of the vial 700 to another element by defining a rib 720 to which the other element can grip or otherwise engage to be in fixed spatial relation with the vial 700. The coupling can be a releasable coupling such that the vial 700 can be removed from the element to which the vial 700 is coupled, e.g., to be replaced with the same or different vial and/or to facilitate disposal of the vial 700 and/or the other element. The coupling can be a fixed coupling such that the vial 700 cannot be removed from the element to which the vial 700 is coupled without breaking the vial 700 and/or the element or otherwise rendering the vial 700 and/or the other element unsuitable for further use. The other element can be a drug delivery device such that the vial 700 is coupled thereto for delivery of the drug 710 out of the drug delivery device. The vial 700 can be releasably coupled or fixedly coupled to the drug delivery device. The other element can be a strip to which one or more of the vials 700 are coupled. The strip may facilitate packaging, branding, and/or transport of the vial(s) 700 and/or may provide a base member as a cartridge strip from which each of the vial(s) 700 can be coupled to the other element.

In other embodiments, the vial 700 can lack one or both of the distal flange 714 and the proximal flange 718.

Figure 10:
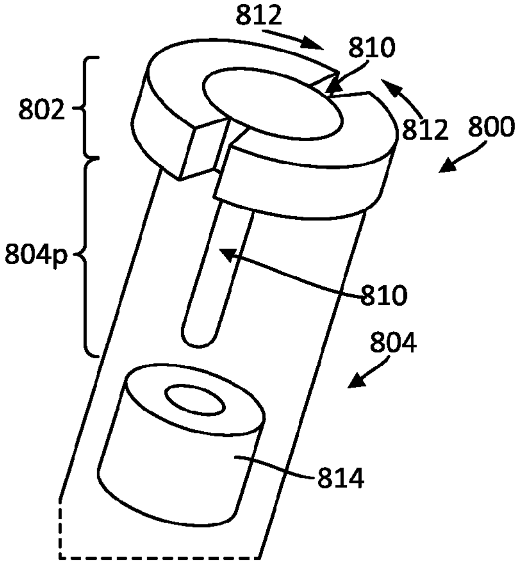
FIG. 10 is a side cross-sectional view of yet another embodiment of a drug holder and a portion of yet another embodiment of the drug delivery device.

FIG. 10 illustrates another exemplary embodiment of the drug holder 102 of FIG. 1 that is configured to be used with the drug delivery device 100 of FIG. 1. The drug holder 800 in this illustrated embodiment is a vial and is generally configured and used similar to the drug holder 200 of FIG. 2. However, in some embodiments, the vial 800 can include a single cavity configured to contain a drug therein instead of including proximal and distal cavities.

The vial 800 in this illustrated embodiment includes a head portion 802 that is resilient and a base portion 804 that is resilient in at least a proximal portion 804*p* thereof. In some embodiments, the entire vial 800 is resilient. The base portion 804 is only partially shown in FIG. 10. The vial 800 in this illustrated embodiment does not include a tapered neck portion. The resiliency of the vial 800, e.g., the resiliency of at least head portion 802 and the proximal portion 804*p* of the base portion 804, is configured to facilitate coupling of the vial 800 to another element. Similar to that discussed above regarding FIG. 9, the other element can be, e.g., a drug delivery device or a strip.

The vial 800 is made from one or more materials configured to allow for the vial 800 to be resilient. For example, the material can be plastic. Plastic may be less expensive than other vial materials such as glass and/or may reduce manufacturing cost of the vial 800 compared to other vial materials such as glass.

The vial 800 includes a pair of slots 810 configured to allow for the vial 800 to be resilient. The slots 810 are thus located in the head portion 802 and in the proximal portion 804*p* of the base portion 804. The slots 810 extend axially along a proximal face of the vial 800, e.g., a proximal face of the head portion 802, and longitudinally along the head portion 802 and the proximal portion 804*p* of the base portion 804. The slots 810 are configured to allow the vial 800 to flex radially inward and outward in the head portion 802 and in the proximal portion 804*p* of the base portion 804. Arrows 812 in FIG. 10 illustrates radially inward flexing. Although the vial 800 in this illustrated embodiment includes two slots 810, the vial 800 can include another number of slots. In an exemplary embodiment, the vial 800 includes a plurality of slots 810 to facilitate even flexing around a perimeter of the vial 800.

FIG. 10 illustrates a seal member 814 disposed in the base portion 804. The seal member 814 is generally configured and used similar to the first seal member 214 of FIG. 2. The seal member 814 is disposed in the base portion 804 distal to the pair of slots 810. In other words, a terminal distal end of the slots 812 is located proximal to the seal member 814. The fluid tight seal provided by the seal member 814 can thus be maintained during the flexing of the head portion 802 and the proximal portion 804*p* of the base portion 804. As in this illustrated embodiment, a central portion of the seal member 814 can be hollow in proximal and distal portions of the seal member 814 with a solid intermediate portion of the seal member 814 being located between the hollow areas. The central portion of the seal member 814 including hollow areas may facilitate passing of a piston, pin, and/or a needle through seal member 814 by providing less material to pass through than if the hollow areas are omitted. The seal member 814 can, however, have a solid central portion or can have only one hollow area either proximal to a solid area or distal to a solid area.

Figure 11:
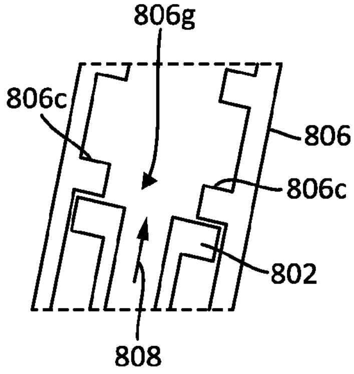
FIG. 11 is a side cross-sectional view of portions of the drug holder and drug delivery device of FIG. 10.

FIG. 11 illustrates an exemplary embodiment in which the vial 800 is coupled to a drug delivery device 806, e.g., the drug delivery device 100 of FIG. 1. An arrow 808 in FIG. 11 illustrates a proximal direction in which the vial 800 can be moved relative to the drug delivery device 806 to be coupled to the drug delivery device 806. The flexing of the vial 800, e.g., in the head portion 802 and in the proximal portion 804*p* of the base portion 804, facilitates proximal movement of the enlarged diameter head portion 802 past an internal coupling feature 806*c* of the drug delivery device 806. The internal coupling feature 806*c* is a circumferential ring that extends radially inward, although in other embodiments the ring can be a broken ring including a plurality of radially-inward extending arc members. The slots 812 allow the vial 800 to automatically flex radially inward as the vial 800 moves through an opening 806*g* and proximally past the coupling feature 806*c*. Then, when the enlarged diameter head portion 802 has passed proximally beyond the coupling feature 806*c*, the slots 812 allow the vial 800 to automatically flex radially outward. The head portion 802 of the vial 800 then cannot move distally past the coupling feature 806*c*, which defines the opening 806*g* that has a diameter that is less than a diameter of the head portion 802 in its non-flexed configuration, which is shown in FIGS. 10 and 11. The vial 800 is thereby coupled to the drug delivery device 800.

Figure 12:
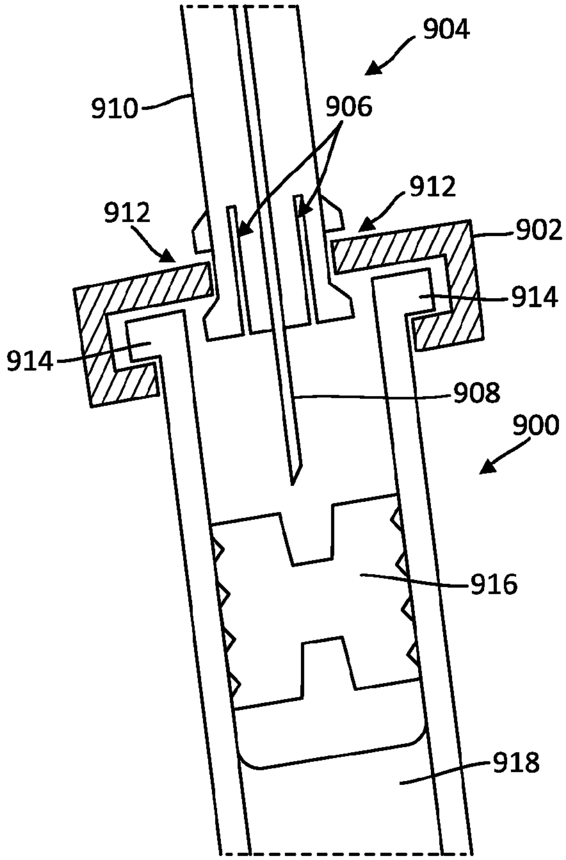
FIG. 12 is a side cross-sectional view of a portion of another embodiment of a drug holder and a portion of another embodiment of the drug delivery device.

FIG. 12 illustrates another exemplary embodiment of the drug holder 102 of FIG. 1 that is configured to be used with the drug delivery device 100 of FIG. 1. The drug holder 900 in this illustrated embodiment is a vial and is generally configured and used similar to the drug holder 200 of FIG. 2. However, in some embodiments, the vial 900 can include a single cavity configured to contain a drug therein instead of including proximal and distal cavities.

The vial 900 in this illustrated embodiment includes a proximal cap 902 configured to facilitate coupling of the vial 900 to a drug delivery device 904. The drug delivery device 904 is generally configured and used similar to the drug delivery device 100 of FIG. 1 except that the drug delivery device 904 in this illustrated embodiment includes a dispensing mechanism that includes a plurality of slots 906 configured to allow for the dispensing mechanism to be resilient. The dispensing mechanism includes a pin 908 and a pin holder 910. The pin holder 910 holds the pin 908 and that has the slots 906 formed therein. The slots 906 extend longitudinally along the pin holder 910 and, more particularly, extend proximally from a distal end of the pin holder 910 along a partial longitudinal length of the drug holder 910. The slots 906 are configured to allow the pin holder 910 to flex radially inward and outward without the pin holder 910 losing its hold of the pin 908. Although the dispensing mechanism in this illustrated embodiment includes four slots 906 (two slots are visible in FIG. 12 with another two slots on an opposite, obscured side of the pin holder 910), the dispensing mechanism can include another number of slots. In an exemplary embodiment, the dispensing mechanism includes a plurality of slots 908 to facilitate even flexing around a perimeter of the dispensing mechanism.

The drug delivery device 904, e.g., the pin holder 910 thereof, includes a distal rib 912 that is configured and used similar to the proximal rib 720 of the vial 700 of FIG. 9. The rib 912 is configured to facilitate coupling of the drug delivery device 904 to a coupling feature of the vial 900, which in this illustrated embodiment is the cap 902 seated over the vial's enlarged diameter head portion 914. The vial's cap 902 is configured to grip or otherwise engage the rib 912 to couple vial 900 and the drug delivery device 904 together. FIG. 12 illustrates the cap 902 clipped to the rib 912 of the pin holder 910. The slots 906 allow for radial inward and outward flexing of the pin holder 910 during coupling of the pin holder 910 to the vial 900 similar to that discussed above regarding the slots 810 of the vial 800 of FIG. 10. The pin holder 910 clipping onto the vial 900 via the rib 912 and cap 902 may help ensure that the needle 908 is correctly positioned relative to the vial 900 to effectively pierce or puncture the vial's seal member 916 and access drug 918 contained in the vial 900 distal to the seal member 916, e.g., in response to the vial 900 being pushed proximally relative to the dispensing mechanism.

Figure 13:
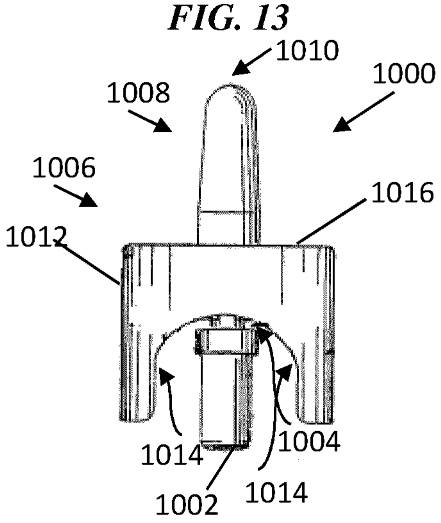
FIG. 13 is a side view of another embodiment of the drug delivery device of FIG. 1.

FIG. 13 illustrates one embodiment of a drug delivery device 1000 that can be used with a drug holder as described herein. The drug delivery device 1000 is generally configured and used similar to the drug delivery device 100 of FIG. 1 and includes a drug holder 1002, a piston 1004, and a dispensing head 1006 including a tip 1008 and an opening 1010. The dispensing head 1006 has the piston 1004 fixed thereto. From an inner end face of the piston 1004 emanates an outlet channel, which is guided in valve-free manner to the opening 1010 leading into the open and which is formed by an atomizing nozzle. The outlet channel becomes to be in fluid communication with a hollow interior of the drug holder 1002 in response to the piston 1004 puncturing or piercing a proximal seal member of the drug holder 1002 as the drug holder 1002 is pushed proximally, e.g., in a direction toward the opening 1010. The dispensing head 1006 includes a handle portion 1012 configured to be handheld. Flattened sides of the handle portion 1012 include two facing finger openings 1014 configured to receive a thumb of a user's hand with the index and middle finger of this hand on either side of a discharge connection of the handle portion 1012 on an outside of the handle portion's end wall 1016 or elsewhere on the handle portion 1012. By moving together the thumb and the two other fingers the drug holder 1002 can be displaced with respect to the piston 1004 or the dispensing head 1006 and the drug consequently sprayed out of the drug holder 1002 through a discharge channel of the drug delivery device 1000 and through the opening 1010. The drug delivery device 1000 is further described in U.S. Pat. No. 4,946,069 entitled "Dispenser For Manually Discharging Flowable Media" issued Aug. 7, 1990, which is hereby incorporated by reference in its entirety.

Figure 14:
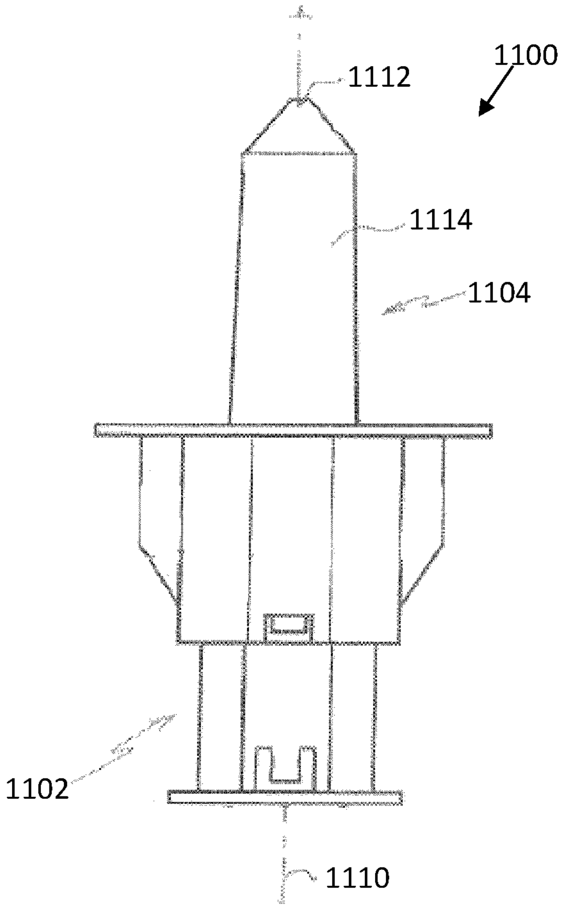
FIG. 14 is a side view of yet another embodiment of the drug delivery device of FIG. 1, the drug delivery device being in a pre use state.
Figure 15:
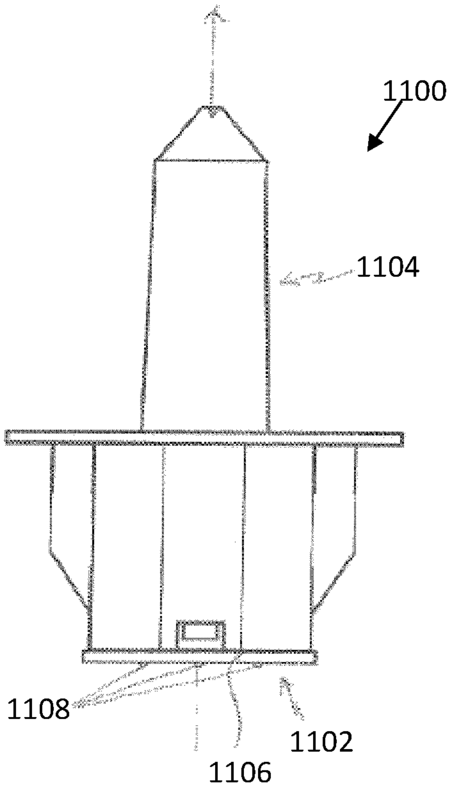
FIG. 15 is a side view of the drug delivery device of FIG. 14 in a post use state.

FIGS. 14 and 15 illustrate another embodiment of a drug delivery device 1100 that can be used with a drug holder as described herein. The drug delivery device 1100 is generally configured and used similar to the drug delivery device 100 of FIG. 1. FIG. 14 shows this illustrated embodiment of a drug delivery device 1100 in an initial or pre-use configuration, and FIG. 15 shows the drug delivery device 1100 in an actuated or post use configuration. In the post use configuration, a body 1102 of the drug delivery device 1100 has been inserted into a dispensing head 1104 of the drug delivery device 1100 such that only an endplate 1106 of the body 1102 is visible.

The body 1102, which includes a drug holder therein, is configured to be inserted into the dispensing head 1104 substantially along a first axis 1110. A person skilled in the art will appreciate that the body 1102 may not be inserted precisely along the first axis 1110 but nevertheless be considered to be inserted substantially along the first axis 1110 due to any number of factors, such as manufacturing tolerances and sensitivity of measurement equipment. The body 1102 defines an actuator of the drug delivery device 1100 that is configured to be manually moved by a user to be inserted into the dispensing head 1104 and cause drug delivery. The endplate 1106 includes a gripping feature 1108 configured to facilitate actuation by increasing grip of the body's surface for a finger of a user. The gripping feature 1108 includes surface projections in this illustrated embodiment but can have other configurations, such as a textured surface, a finger depression, etc.

During use of the drug delivery device 1100, an insertion force is applied to the body 1102 such that the body 1102 slides proximally, e.g., toward an opening 1112 in a tip 1114 of the dispensing head 1104, relative to the dispensing head 1104. As the body 1102 is moved in the proximal direction, a piercing element punctures or pierces a proximal seal member of the drug holder. Further movement of the body 1102 in the proximal direction causes a piercer stop of a holder holding the piercing element in the dispensing head 1104 to come into contact with the drug holder. The contact between the piercer stop and the drug holder configured to prevent further insertion of the body 1102 in the proximal direction, which can act as an indicator to a user of the drug delivery device 1100 that actuation has been completed.

The drug delivery device 1100 is further described in U.S. Pat. Pub. No. 2018/0361085 entitled "Nasal Spray Assembly" published Dec. 20, 2018, which is hereby incorporated by reference in its entirety.

Figure 16:
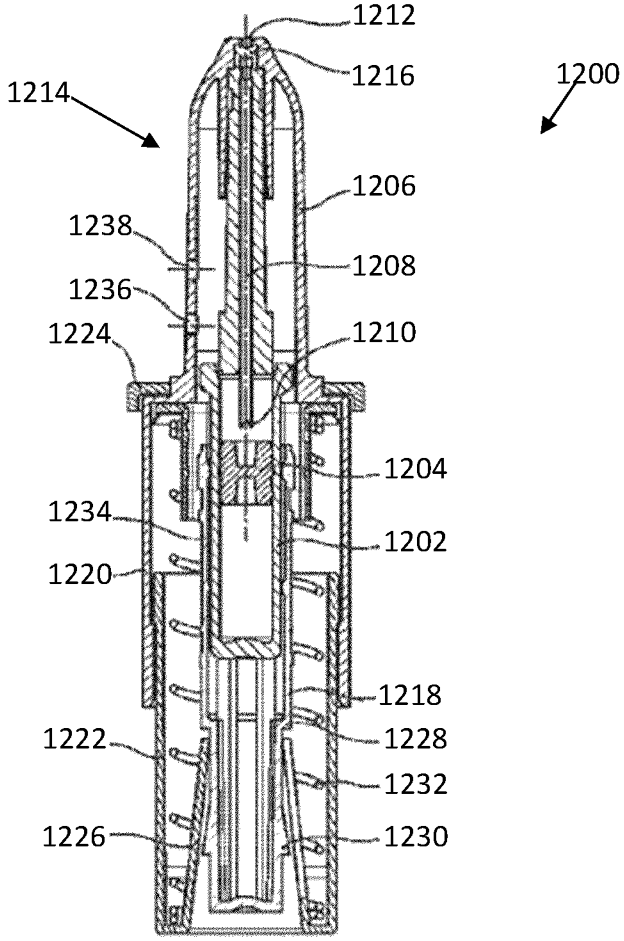
FIG. 16 is a side cross-sectional view of still another embodiment of the drug delivery device of FIG. 1.

FIG. 16 illustrates one embodiment of a drug delivery device 1200 that can be used with a drug holder as described herein. The drug delivery device 1200 is generally configured and used similar to the drug delivery device 100 of FIG. 1 and includes a drug holder 1202 containing two doses of drug therein. A dispensing mechanism, such as a piston 1204, is mounted to slide in the drug holder 1202. In a pre-actuation position of the drug delivery device 1200, shown in FIG. 16, the piston 1204 acts as a stopper, isolating the drug. The drug delivery device 1200 also includes a dispensing head 1206 that is assembled on the drug holder 1202 and that is configured to be axially movable relative to the drug holder 1202. In particular, an axial movement of the dispensing head 1206 relative to the drug holder 1202 causes the piston 1204 to move in the drug holder 1202, and thus causes the drug contained in the drug holder 1202 to be dispensed. The dispensing head 1206 includes a dispenser channel 1208 that extends from a perforator tip 1210 to an opening 1212 in a tip 1214 of the dispensing head 1206. Proximal to or upstream of the opening 1212, a spray chamber 1216 can be provided that is configured to facilitate dispensing of the drug as a spray.

The drug holder 1202 is fastened in a body 1218 that is thus secured to the drug holder 1202 and that moves together with the drug holder 1202.

The dispensing head 1206 includes a bottom side skirt 1220 that is adapted to cooperate with an actuator 1222 of the drug delivery device 1200. A finger-rest element 1224 can be assembled around the dispensing head 1206 or can be formed integrally therewith.

The actuator 1222 is configured to be axially movable inside the side skirt 1220 of the dispensing head 1206 so as to perform successive actuations of the drug delivery device 1200. The actuator 1222 includes at least one sloping tab 1226 that is configured to cooperate with projections 1228, 1230 of the body 1218 so as to perform successive actuations. A return spring 1232 is mounted between the actuator 1222 and the dispensing head 1206 so as to return the actuator 1222 into its start position after each actuation.

The drug delivery device 1200 includes a device indicator 1234 configured to indicate to a user whether a first dose has been dispensed and whether a second dose has been dispensed. In this way, the user knows exactly what the situation is, and whether or not the first dose has been dispensed. The indicator 1234 is configured to cooperate with viewing windows 1236, 1238 that are formed in the dispensing head 1206. The viewing windows 1236, 1238 are formed in a side wall of the dispensing head 1206, clearly visible to the user when the drug delivery device 1200 is held in the hand.

The drug delivery device 1200 is further described in U.S. Pat. No. 9,555,950 entitled "Fluid Product Dispensing Device" issued Jan. 31, 2017, which is hereby incorporated by reference in its entirety.

Embodiments of nasal drug delivery devices disclosed herein can be designed to be disposed of after a single use, or they can be designed to be used multiple times. In either case, in at least some embodiments, the drug delivery device can be reconditioned for reuse after at least one use. Reconditioning can include any combination of the steps of disassembly of the drug delivery device, followed by cleaning or replacement of particular pieces and subsequent reassembly. In particular, the drug delivery device can be disassembled, and any number of the particular pieces or parts of the drug delivery device can be selectively replaced or removed in any combination. Upon cleaning and/or replacement of particular parts, the drug delivery device can be reassembled for subsequent use either at a reconditioning facility, or by a health care provider immediately prior to use. A person skilled in the art will appreciate that reconditioning of a drug delivery device can utilize a variety of techniques for disassembly, cleaning/replacement, and reassembly. Use of such techniques, and the resulting reconditioned drug delivery device, are all within the scope of the present application.

The present disclosure has been described above by way of example only within the context of the overall disclosure provided herein. It will be appreciated that modifications within the spirit and scope of the claims may be made without departing from the overall scope of the present disclosure.

What is claimed is:

1. A drug delivery system, comprising:
- a drug holder configured to be coupled to a drug delivery device, the drug holder comprising:
  - a first cavity configured to contain either a first drug or air therein,
  - a second cavity configured to contain either a second drug or air therein, and
  - a seal member located between the first and second cavities, configured to provide a fluid seal between the first and second cavities, and configured to be broken by a nasal drug delivery device to break the fluid seal; and
- the nasal drug delivery device comprising:
  - a tip configured to be positioned in a nose of a patient, the tip having an opening therein; and
  - an actuator that is configured to be actuated in a first actuation to cause delivery of the first drug or air through the opening without causing delivery of the second drug or air through the opening, and that is configured to be actuated in a second actuation to cause delivery of the second drug or air through the opening.

2. The system of claim 1, wherein the drug holder comprises a head portion and a body portion that is distal to the head portion;
- the first and second cavities are each in the body portion; and
- the seal member is located in the body portion between the first and second cavities.

3. The system of claim 1, wherein the drug holder includes a vial.

4. The system of claim 1, wherein the first cavity contains the first drug, and the second cavity contains the second drug.

5. The system of claim 4, wherein the first drug is one of ketamine, esketamine, naloxone, and sumatriptanl, and the second drug is one of ketamine, esketamine, naloxone, and sumatriptanl.

6. The system of claim 5, wherein the first drug and the second drug are the same.

7. The system of claim 5, wherein the first drug and the second drug are different.

8. The system of claim 1, wherein the seal member is configured to be broken by being pierced or punctured by at least one of a piston, a pin, and a needle of the nasal drug delivery device.

9. A drug product disposed in the drug holder of claim 1, wherein the drug product is one of ketamine, esketamine, naloxone, and sumatriptan.

10. A drug delivery method, comprising:

actuating the drug delivery device of claim 4 to cause a plunger to push the first drug out of an opening formed in the drug delivery device; and after the first drug has been pushed out of the opening, actuating the drug delivery device again to cause the plunger to push the second drug out of the opening.

11. The method of claim 10, wherein the first drug is one of ketamine, esketamine, naloxone, and sumatriptanl, and the second drug is one of ketamine, esketamine, naloxone, and sumatriptanl.

12. The system of claim 1, wherein the first cavity contains the first drug, the second cavity contains air, and the first cavity is distal to the second cavity.

13. A drug delivery method, comprising:

actuating the drug delivery device of claim 12 to cause a plunger to push both the first drug and the air out of an opening formed in the drug delivery device.

14. The method of claim 13, wherein the first drug is one of ketamine, esketamine, naloxone, and sumatriptanl.

15. The system of claim 1, wherein the first cavity contains air, the second cavity contains the second drug, and the first cavity is distal to the second cavity.

16. The system of claim 15, wherein the second drug is one of ketamine, esketamine, naloxone, and sumatriptan.

17. A drug delivery method, comprising:

actuating the drug delivery device of claim 15 to cause a plunger to push both the second drug and the air out of an opening formed in the drug delivery device.

18. The method of claim 17, wherein the first drug is one of ketamine, esketamine, naloxone, and sumatriptan.

19. The system of claim 1, further comprising a second seal member located proximal to the first and second cavities and configured to be broken by a drug delivery device to break a fluid seal provided by the second seal member.

20. The system of claim 1, wherein the first cavity contains the first drug, and the second cavity contains the second drug.

21. The system of claim 20, the first drug is one of ketamine, esketamine, naloxone, and sumatriptanl, and the second drug is one of ketamine, esketamine, naloxone, and sumatriptanl.

22. The system of claim 21, wherein the first drug and the second drug are the same.

23. The system of claim 21, wherein the first drug and the second drug are different.

24. A drug delivery system, comprising:

a nasal drug delivery device, wherein the nasal delivery device comprises a tip configured to be positioned in a nose of a patient, the tip having an opening therein; and a drug holder configured to be coupled to a drug delivery device, the drug holder comprising:

a first cavity configured to contain either a first drug or air therein, a second cavity configured to contain either a second drug or air therein, and a seal member located between the first and second cavities, configured to provide a fluid seal between the first and second cavities, and configured to be broken by the nasal drug delivery device to break the fluid seal, wherein the first cavity contains the first drug, the second cavity contains air, and the drug delivery device is configured to simultaneously deliver the first drug and the air through the opening.

25. The system of claim 24, wherein the first drug is one of ketamine, esketamine, naloxone, and sumatriptanl.

26. A drug delivery system, comprising:

a drug holder comprising a first blister seal and a second blister seal, the drug holder being configured to hold a drug between the first and second blister seals, and the first blister seal being distal to the second blister seal; and a nasal drug delivery device comprising a proximal tip configured to be positioned in a nose of a patient, the tip having an opening therein, and an actuator configured to be actuated to break the first blister seal and thereby create a force that causes the second blister seal to break and the drug to be delivered out of the opening.

27. The system of claim 26, wherein the actuator includes a plunger configured to be actuated by moving proximally relative to the proximal tip.

28. The system of claim 27, wherein the drug holder is located between the opening and the plunger.

29. The system of claim 26, wherein the drug is one of ketamine, esketamine, naloxone, and sumatriptan.

30. A drug product disposed in the system of claim 26, wherein the drug product is one of ketamine, esketamine, naloxone, and sumatriptan.

31. The system of claim 15, wherein the first drug is one of ketamine, esketamine, naloxone, and sumatriptan.

* * * * *